United States Patent
Gerber et al.

(10) Patent No.: US 9,700,661 B2
(45) Date of Patent: Jul. 11, 2017

(54) CHRONIC PH OR ELECTROLYTE MONITORING

(75) Inventors: Martin Gerber, Maple Grove, MN (US); Suping Lyu, Maple Grove, MN (US); Bryant Pudil, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 708 days.

(21) Appl. No.: 13/424,525

(22) Filed: Mar. 20, 2012

(65) Prior Publication Data

US 2012/0277552 A1    Nov. 1, 2012

Related U.S. Application Data

(60) Provisional application No. 61/480,539, filed on Apr. 29, 2011, provisional application No. 61/480,544, (Continued)

(51) Int. Cl.
*A61M 1/00* (2006.01)
*A61M 31/00* (2006.01)
(Continued)

(52) U.S. Cl.
CPC .......... *A61M 1/1603* (2014.02); *A61B 5/0031* (2013.01); *A61B 5/026* (2013.01);
(Continued)

(58) Field of Classification Search
CPC ........ B01D 11/00; B01D 61/00; B01D 21/30; B01D 61/08; B01D 61/12; B01D 61/32; B01D 65/02; C02F 1/44; A61B 5/00; A61B 5/02; A61B 5/0031; A61B 5/142; A61B 5/201; A61B 5/208; A61B 5/1485; A61B 5/14503; A61B 5/14532; A61B 5/14539;
(Continued)

(56) References Cited

U.S. PATENT DOCUMENTS 3,608,729 A    9/1971   Haselden
3,669,878 A    6/1972   Marantz
(Continued)

FOREIGN PATENT DOCUMENTS

CN    103037917    4/2013
EP     266795 A2   11/1987
(Continued)

OTHER PUBLICATIONS

International Search Report, PCT/US2012/034330 mailed Aug. 28, 2012.
(Continued)

*Primary Examiner* — Dirk Bass
*Assistant Examiner* — Hayden Brewster
(74) *Attorney, Agent, or Firm* — Kenneth Collier; Roger Hahn

(57) ABSTRACT

Methods include monitoring blood pH or electrolyte levels and setting initial fluid parameters, such as dialysate fluid parameters or replacement fluid parameters, for a blood fluid removal session based the monitored data. Blood fluid removal systems may employ sensors that monitor blood pH or electrolyte levels to adjust the fluid parameters during a blood fluid removal session.

24 Claims, 7 Drawing Sheets

Related U.S. Application Data filed on Apr. 29, 2011, provisional application No. 61/480,541, filed on Apr. 29, 2011, provisional application No. 61/480,535, filed on Apr. 29, 2011, provisional application No. 61/480,532, filed on Apr. 29, 2011, provisional application No. 61/480,530, filed on Apr. 29, 2011, provisional application No. 61/480,528, filed on Apr. 29, 2011.

(51) Int. Cl.

| | | |
|---|---|---|
| *A61M 37/00* | (2006.01) | |
| *A61B 5/00* | (2006.01) | |
| *B01D 61/00* | (2006.01) | |
| *A61M 1/16* | (2006.01) | |
| *A61B 5/145* | (2006.01) | |
| *A61B 5/026* | (2006.01) | |
| *A61B 5/053* | (2006.01) | |
| *A61M 1/34* | (2006.01) | |
| *B01D 65/02* | (2006.01) | |
| *A61B 5/0295* | (2006.01) | |
| *A61M 1/14* | (2006.01) | |
| *B01D 61/32* | (2006.01) | |
| *A61M 1/36* | (2006.01) | |
| *A61M 1/28* | (2006.01) | |
| *B01D 11/00* | (2006.01) | |

(52) U.S. Cl.
CPC ............ *A61B 5/0295* (2013.01); *A61B 5/053* (2013.01); *A61B 5/0537* (2013.01); *A61B 5/145* (2013.01); *A61B 5/14503* (2013.01); *A61B 5/14535* (2013.01); *A61B 5/14539* (2013.01); *A61B 5/14546* (2013.01); *A61B 5/4836* (2013.01); *A61B 5/4848* (2013.01); *A61B 5/4875* (2013.01); *A61B 5/6866* (2013.01); *A61B 5/7282* (2013.01); *A61M 1/00* (2013.01); *A61M 1/14* (2013.01); *A61M 1/16* (2013.01); *A61M 1/1601* (2014.02); *A61M 1/1605* (2014.02); *A61M 1/1607* (2014.02); *A61M 1/1613* (2014.02); *A61M 1/28* (2013.01); *A61M 1/34* (2013.01); *A61M 1/342* (2013.01); *A61M 1/3607* (2014.02); *A61M 1/3609* (2014.02); *A61M 1/3672* (2013.01); *B01D 61/00* (2013.01); *B01D 61/32* (2013.01); *B01D 65/02* (2013.01); *A61B 2560/0223* (2013.01); *A61M 2202/0498* (2013.01); *A61M 2205/04* (2013.01); *A61M 2205/18* (2013.01); *A61M 2205/33* (2013.01); *A61M 2205/3303* (2013.01); *A61M 2205/3334* (2013.01); *A61M 2205/3523* (2013.01); *A61M 2205/50* (2013.01); *A61M 2205/52* (2013.01); *A61M 2205/60* (2013.01); *A61M 2205/70* (2013.01); *A61M 2230/00* (2013.01); *A61M 2230/005* (2013.01); *A61M 2230/20* (2013.01); *A61M 2230/207* (2013.01); *A61M 2230/208* (2013.01); *A61M 2230/65* (2013.01); *B01D 2321/12* (2013.01); *B01D 2321/40* (2013.01)

(58) Field of Classification Search
CPC . A61B 5/14546; A61B 5/1723; A61B 5/4839; A61B 5/0002; A61B 5/0006; A61B 5/0205; A61B 5/0215; A61B 5/02225; A61B 5/021; A61B 5/022; A61B 5/024; A61B 5/026; A61B 5/0295; A61B 5/0428; A61B 5/0452; A61B 5/053; A61B 5/0537; A61B 5/145; A61B 5/14535; A61B 5/222; A61B 5/486; A61B 5/4836; A61B 5/4848; A61B 5/4875; A61B 5/6866; A61B 5/7282; A61B 2560/0223; A61M 1/00; A61M 1/14; A61M 1/16; A61M 1/1601; A61M 1/1603; A61M 1/1605; A61M 1/1607; A61M 1/1609; A61M 1/1611; A61M 1/1613; A61M 1/1615; A61M 1/1647; A61M 1/28; A61M 1/34; A61M 1/341; A61M 1/3403; A61M 1/342; A61M 1/3472; A61M 1/3609; A61M 1/3643; A61M 1/3672; A61M 1/3679; A61M 1/5607; A61M 1/656; A61M 5/142; A61M 5/1723; A61M 31/00; A61M 37/00; A61M 2001/165; A61M 2001/1666; A61M 2001/3437; A61M 2205/04; A61M 2205/18; A61M 2205/33; A61M 2205/3303; A61M 2205/3334; A61M 2205/3523; A61M 2205/50; A61M 2205/52; A61M 2205/60; A61M 2205/70; A61M 2230/00; A61M 2230/005; A61M 2230/20; A61M 2230/207; A61M 2230/208; A61M 2230/65; A61K 33/14
USPC .............. 210/647, 96.2, 143, 645, 646, 739; 800/309, 377, 381; 600/309, 377, 381, 600/300, 483, 485, 508
See application file for complete search history.

(56) References Cited

U.S. PATENT DOCUMENTS

| | | |
|---|---|---|
| 3,669,880 A | 6/1972 | Marantz |
| 3,850,835 A | 11/1974 | Marantz |
| 3,884,808 A | 5/1975 | Scott |
| 3,989,622 A | 11/1976 | Marantz |
| 4,060,485 A | 11/1977 | Eaton |
| 4,371,385 A | 2/1983 | Johnson |
| 4,374,382 A | 2/1983 | Markowitz |
| 4,381,999 A | 5/1983 | Boucher |
| 4,460,555 A | 7/1984 | Thompson |
| 4,556,063 A | 12/1985 | Thompson et al. |
| 4,562,751 A | 1/1986 | Nason |
| 4,581,141 A | 4/1986 | Ash |
| 4,650,587 A | 3/1987 | Polak |
| 4,678,408 A | 7/1987 | Nason |
| 4,685,903 A | 8/1987 | Cable |
| 4,750,494 A | 6/1988 | King et al. |
| 4,826,663 A | 5/1989 | Alberti |
| 4,828,693 A | 5/1989 | Lindsay |
| 5,080,653 A | 1/1992 | Voss |
| 5,091,094 A * | 2/1992 | Veech .................. A61M 1/1656 210/321.71 |
| 5,092,886 A | 3/1992 | Dobos-Hardy |
| 5,097,122 A | 3/1992 | Colman |
| 5,127,404 A | 7/1992 | Wyborny et al. |
| 5,284,470 A | 2/1994 | Beltz |
| 5,302,288 A | 4/1994 | Meidl |
| 5,305,745 A | 4/1994 | Zacouto et al. |
| 5,318,750 A | 6/1994 | Lascombes |
| 5,468,388 A | 11/1995 | Goddard |
| 5,683,432 A | 11/1997 | Goedeke et al. |
| 5,762,782 A | 6/1998 | Kenley |
| 5,902,336 A * | 5/1999 | Mishkin ..................... 623/11.11 |
| 5,944,684 A | 8/1999 | Roberts |
| 6,048,732 A | 4/2000 | Anslyn |
| 6,052,622 A | 4/2000 | Holmstrom |
| 6,058,331 A | 5/2000 | King |
| 6,156,002 A | 12/2000 | Polaschegg et al. |
| 6,230,059 B1 | 5/2001 | Duffin |
| 6,248,093 B1 | 6/2001 | Moberg |
| 6,254,567 B1 | 7/2001 | Treu |
| 6,321,101 B1 | 11/2001 | Holmstrom |
| 6,362,591 B1 | 3/2002 | Moberg |
| 6,363,279 B1 | 3/2002 | Ben-Haim et al. |

(56) References Cited

U.S. PATENT DOCUMENTS

| | | |
|---|---|---|
| 6,505,075 B1 | 1/2003 | Weiner |
| 6,554,798 B1 | 4/2003 | Mann |
| 6,555,986 B2 | 4/2003 | Moberg |
| 6,561,996 B1 * | 5/2003 | Gorsuch ............. 604/6.09 |
| 6,589,229 B1 | 7/2003 | Connelly |
| 6,602,399 B1 | 8/2003 | Fromherz et al. |
| 6,627,164 B1 | 9/2003 | Wong |
| 6,676,608 B1 | 1/2004 | Keren |
| 6,689,083 B1 | 2/2004 | Gelfand |
| 6,706,007 B2 | 3/2004 | Gelfand |
| 6,711,439 B1 | 3/2004 | Bradley et al. |
| 6,726,647 B1 | 4/2004 | Sternby |
| 6,780,322 B1 | 8/2004 | Bissler |
| 6,818,196 B2 | 11/2004 | Wong |
| 6,878,283 B2 | 4/2005 | Thompson |
| 6,887,214 B1 | 5/2005 | Levin |
| 6,890,315 B1 | 5/2005 | Levin |
| 6,960,179 B2 | 11/2005 | Gura |
| 7,074,332 B2 | 7/2006 | Summerton |
| 7,077,819 B1 | 7/2006 | Goldau Rainer et al. |
| 7,175,809 B2 | 2/2007 | Gelfand |
| 7,208,092 B2 | 4/2007 | Micheli |
| 7,276,042 B2 | 10/2007 | Polaschegg |
| 7,399,289 B2 | 7/2008 | Gelfand |
| 7,500,958 B2 | 3/2009 | Asbrink |
| 7,566,432 B2 | 7/2009 | Wong |
| 7,575,564 B2 | 8/2009 | Childers |
| 7,674,231 B2 | 3/2010 | McCombie |
| 7,704,361 B2 | 4/2010 | Garde |
| 7,736,507 B2 | 6/2010 | Wong |
| 7,744,553 B2 | 6/2010 | Kelly |
| 7,754,852 B2 | 7/2010 | Burnett |
| 7,756,572 B1 | 7/2010 | Fard |
| 7,775,983 B2 | 8/2010 | Zhang |
| 7,776,210 B2 | 8/2010 | Rosenbaum et al. |
| 7,785,463 B2 | 8/2010 | Bissler |
| 7,794,141 B2 | 9/2010 | Perry |
| 7,850,635 B2 | 12/2010 | Polaschegg |
| 7,857,976 B2 | 12/2010 | Bissler |
| 7,867,214 B2 | 1/2011 | Childers |
| 7,896,831 B2 | 3/2011 | Sternby |
| 7,922,686 B2 | 4/2011 | Childers |
| 7,922,911 B2 | 4/2011 | Micheli |
| 7,947,179 B2 | 5/2011 | Rosenbaum et al. |
| 7,955,291 B2 | 6/2011 | Sternby |
| 7,967,022 B2 | 6/2011 | Grant |
| 7,981,082 B2 | 7/2011 | Wang |
| 8,034,161 B2 | 10/2011 | Gura |
| 8,070,709 B2 | 12/2011 | Childers |
| 8,096,969 B2 | 1/2012 | Roberts |
| 8,183,046 B2 | 5/2012 | Lu |
| 8,187,250 B2 | 5/2012 | Roberts |
| 8,197,439 B2 | 6/2012 | Wang |
| 8,202,241 B2 | 6/2012 | Karakama |
| 8,246,826 B2 | 8/2012 | Wilt |
| 8,273,049 B2 | 9/2012 | Demers |
| 8,282,828 B2 | 10/2012 | Wallenas |
| 8,292,594 B2 | 10/2012 | Tracey |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,404,091 B2 | 3/2013 | Ding |
| 8,409,441 B2 | 4/2013 | Wilt |
| 8,496,809 B2 | 7/2013 | Roger |
| 8,499,780 B2 | 8/2013 | Wilt |
| 8,500,676 B2 | 8/2013 | Jansson |
| 8,512,271 B2 | 8/2013 | Moissl |
| 8,518,260 B2 | 8/2013 | Raimann |
| 8,521,482 B2 | 8/2013 | Akonur |
| 8,535,525 B2 | 9/2013 | Heyes |
| 8,560,510 B2 | 10/2013 | Brueggerhoff |
| 8,580,112 B2 | 11/2013 | Updyke |
| 8,597,227 B2 | 12/2013 | Childers |
| 8,696,626 B2 | 4/2014 | Kirsch |
| 8,903,492 B2 | 12/2014 | Soykan |
| 2002/0042561 A1 | 4/2002 | Schulman |
| 2002/0112609 A1 | 8/2002 | Wong |
| 2003/0080059 A1 | 5/2003 | Peterson |
| 2003/0097086 A1 | 5/2003 | Gura |
| 2003/0105435 A1 | 6/2003 | Taylor |
| 2003/0114787 A1 | 6/2003 | Gura |
| 2003/0216677 A1 * | 11/2003 | Pan ............. A61M 1/1609 604/5.04 |
| 2004/0019312 A1 * | 1/2004 | Childers et al. ............. 604/4.01 |
| 2004/0068219 A1 | 4/2004 | Summerton |
| 2004/0099593 A1 | 5/2004 | DePaolis |
| 2004/0147872 A1 * | 7/2004 | Thompson ............. 604/67 |
| 2004/0147900 A1 | 7/2004 | Polaschegg |
| 2004/0168969 A1 | 9/2004 | Sternby |
| 2004/0215090 A1 | 10/2004 | Erkkila |
| 2005/0065760 A1 | 3/2005 | Murtfeldt |
| 2005/0113796 A1 | 5/2005 | Taylor |
| 2005/0126961 A1 | 6/2005 | Bissler |
| 2005/0126998 A1 | 6/2005 | Childers |
| 2005/0131331 A1 | 6/2005 | Kelly |
| 2005/0150832 A1 | 7/2005 | Tsukamoto |
| 2005/0234381 A1 | 10/2005 | Niemetz |
| 2005/0236330 A1 | 10/2005 | Nier et al. |
| 2005/0274658 A1 | 12/2005 | Rosenbaum et al. |
| 2006/0025661 A1 | 2/2006 | Sweeney |
| 2006/0025748 A1 * | 2/2006 | Ye ............. 604/503 |
| 2006/0058731 A1 | 3/2006 | Burnett |
| 2006/0195064 A1 | 8/2006 | Plahey |
| 2006/0217771 A1 | 9/2006 | Soykan et al. |
| 2006/0226079 A1 | 10/2006 | Mori |
| 2006/0241709 A1 | 10/2006 | Soykan |
| 2006/0264894 A1 | 11/2006 | Moberg |
| 2007/0007208 A1 | 1/2007 | Brugger |
| 2007/0066928 A1 | 3/2007 | Lannoy |
| 2007/0138011 A1 | 6/2007 | Hofmann |
| 2007/0175827 A1 | 8/2007 | Wariar |
| 2007/0179431 A1 | 8/2007 | Roberts et al. |
| 2007/0213653 A1 | 9/2007 | Childers |
| 2007/0215545 A1 | 9/2007 | Bissler |
| 2007/0255250 A1 | 11/2007 | Moberg |
| 2008/0006570 A1 | 1/2008 | Gura |
| 2008/0021337 A1 | 1/2008 | Li et al. |
| 2008/0053905 A9 | 3/2008 | Brugger |
| 2008/0067132 A1 | 3/2008 | Ross |
| 2008/0093276 A1 | 4/2008 | Roger |
| 2008/0215247 A1 | 9/2008 | Tonelli |
| 2008/0253427 A1 | 10/2008 | Kamen |
| 2009/0020471 A1 | 1/2009 | Tsukamoto |
| 2009/0101577 A1 | 4/2009 | Fulkerson |
| 2009/0124963 A1 | 5/2009 | Hogard |
| 2009/0127193 A1 | 5/2009 | Updyke |
| 2009/0171261 A1 | 7/2009 | Sternby |
| 2009/0264776 A1 | 10/2009 | Vardy |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0314063 A1 | 12/2009 | Sternby |
| 2010/0004588 A1 | 1/2010 | Yeh |
| 2010/0010429 A1 | 1/2010 | Childers |
| 2010/0042035 A1 | 2/2010 | Moissl |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0113891 A1 | 5/2010 | Barrett |
| 2010/0114012 A1 | 5/2010 | Sandford |
| 2010/0137693 A1 | 6/2010 | Porras |
| 2010/0137782 A1 | 6/2010 | Jansson |
| 2010/0168546 A1 | 7/2010 | Kamath |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |

(56) References Cited

U.S. PATENT DOCUMENTS

| | | |
|---|---|---|
| 2010/0298670 A1* | 11/2010 | Bharmi ............... A61B 5/042 600/309 |
| 2011/0017665 A1 | 1/2011 | Updyke |
| 2011/0048949 A1 | 3/2011 | Ding et al. |
| 2011/0066043 A1 | 3/2011 | Banet |
| 2011/0071465 A1 | 3/2011 | Wang |
| 2011/0077574 A1 | 3/2011 | Sigg et al. |
| 2011/0079558 A1 | 4/2011 | Raimann |
| 2011/0087187 A1 | 4/2011 | Beck |
| 2011/0100909 A1 | 5/2011 | Stange |
| 2011/0106003 A1 | 5/2011 | Childers |
| 2011/0130666 A1 | 6/2011 | Dong et al. |
| 2011/0144570 A1 | 6/2011 | Childers |
| 2011/0184340 A1 | 7/2011 | Tan |
| 2011/0272337 A1 | 11/2011 | Palmer |
| 2011/0301447 A1 | 12/2011 | Park |
| 2012/0016228 A1 | 1/2012 | Kroh |
| 2012/0083729 A1 | 4/2012 | Childers |
| 2012/0085707 A1 | 4/2012 | Beiriger |
| 2012/0115248 A1 | 5/2012 | Ansyln |
| 2012/0220528 A1 | 8/2012 | VanAntwerp |
| 2012/0258546 A1 | 10/2012 | Marran |
| 2012/0259276 A1 | 10/2012 | Childers |
| 2012/0273415 A1 | 11/2012 | Gerber |
| 2012/0273420 A1 | 11/2012 | Gerber |
| 2012/0277546 A1 | 11/2012 | Soykan et al. |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2013/0037465 A1 | 2/2013 | Heyes |
| 2013/0062265 A1 | 3/2013 | Balschat |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228517 A1 | 9/2013 | Roger |
| 2013/0231607 A1 | 9/2013 | Roger |
| 2013/0248426 A1 | 9/2013 | Pouchoulin |
| 2013/0274642 A1 | 10/2013 | Soykan |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan et al. |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2015/0032023 A1 | 1/2015 | Soykan |
| 2015/0080682 A1 | 3/2015 | Gerber |
| 2015/0088047 A1 | 3/2015 | Gerber |
| 2015/0144539 A1 | 5/2015 | Pudil |
| 2015/0250427 A1 | 9/2015 | Soykan |
| 2015/0352269 A1 | 12/2015 | Gerber |
| 2015/0367054 A1 | 12/2015 | Gerber |
| 2016/0206801 A1 | 7/2016 | Gerber |
| 2016/0331884 A1 | 11/2016 | Sigg |

FOREIGN PATENT DOCUMENTS

| | | |
|---|---|---|
| EP | 1124599 | 5/2000 |
| EP | 1175238 | 11/2000 |
| EP | 2308526 | 10/2003 |
| EP | 1364666 A1 | 11/2003 |
| EP | 1523347 | 1/2004 |
| EP | 1523350 | 1/2004 |
| EP | 0906768 | 2/2004 |
| EP | 1691863 | 4/2005 |
| EP | 2116269 | 2/2008 |
| EP | 1450879 | 10/2008 |
| EP | 1514562 | 4/2009 |
| EP | 2219703 | 5/2009 |
| EP | 1592494 B1 | 6/2009 |
| EP | 2100553 A1 | 9/2009 |
| EP | 2398529 | 11/2010 |
| EP | 2575827 A2 | 12/2010 |
| EP | 2100553 | 8/2011 |
| EP | 2576453 A2 | 12/2011 |
| EP | 2701580 | 11/2012 |
| EP | 2701595 | 11/2012 |
| EP | 1345856 B1 | 3/2013 |
| EP | 2344220 B1 | 4/2013 |
| EP | 1351756 | 7/2013 |
| EP | 2190498 | 7/2013 |
| EP | 2701596 | 3/2014 |
| EP | 1582226 | 1/2016 |
| JP | 2002542900 | 12/2002 |
| JP | 2003235965 | 8/2003 |
| WO | 9503839 | 2/1995 |
| WO | 9937342 | 7/1999 |
| WO | 0057935 | 10/2000 |
| WO | 0066197 | 11/2000 |
| WO | 0066197 A1 | 11/2000 |
| WO | 0170307 A1 | 9/2001 |
| WO | 0185295 A2 | 9/2001 |
| WO | 0185295 | 11/2001 |
| WO | 0185295 A2 | 11/2001 |
| WO | 03043677 A2 | 5/2003 |
| WO | 03043680 | 5/2003 |
| WO | 03051422 A2 | 6/2003 |
| WO | 2004008826 | 1/2004 |
| WO | 2004009156 | 1/2004 |
| WO | 2004009158 | 1/2004 |
| WO | 2004030716 A2 | 4/2004 |
| WO | 2004030717 A2 | 4/2004 |
| WO | 2004064616 A2 | 8/2004 |
| WO | 2005061026 | 7/2005 |
| WO | 2005123230 A2 | 12/2005 |
| WO | 2006011009 | 2/2006 |
| WO | 2006017446 | 2/2006 |
| WO | 2007038347 | 4/2007 |
| WO | 2007089855 A2 | 8/2007 |
| WO | 2008037410 | 4/2008 |
| WO | 2009024566 | 2/2009 |
| WO | 2009026603 | 3/2009 |
| WO | 2009026603 A1 | 3/2009 |
| WO | 2009061608 | 5/2009 |
| WO | 2009094184 | 7/2009 |
| WO | 2009157877 | 12/2009 |
| WO | 2009157878 | 12/2009 |
| WO | 2010028860 A1 | 3/2010 |
| WO | 2010033699 | 3/2010 |
| WO | 2010077851 | 7/2010 |
| WO | 2010096659 | 10/2010 |
| WO | 2010121820 | 10/2010 |
| WO | 2011025705 A1 | 3/2011 |
| WO | 2011026645 | 3/2011 |
| WO | 2011137693 | 11/2011 |
| WO | 2012042323 | 4/2012 |
| WO | 2012050781 | 4/2012 |
| WO | 2012051996 | 4/2012 |
| WO | 201202073420 | 7/2012 |
| WO | 2012148781 | 11/2012 |
| WO | 2012148786 | 11/2012 |
| WO | 2012148787 A1 | 11/2012 |
| WO | 2012148789 | 11/2012 |
| WO | 2012162515 A2 | 11/2012 |
| WO | 2012172398 | 12/2012 |
| WO | 2013019179 A1 | 2/2013 |
| WO | 2013019994 | 2/2013 |
| WO | 2013025844 | 2/2013 |
| WO | 2013028809 A3 | 2/2013 |

(56) References Cited

FOREIGN PATENT DOCUMENTS

| WO | 2013101292 | | 7/2013 |
|---|---|---|---|
| WO | 2013103607 | A1 | 7/2013 |
| WO | 2013103906 | | 7/2013 |
| WO | 2013110906 | | 8/2013 |
| WO | 2013110919 | | 8/2013 |
| WO | 2013114063 | A | 8/2013 |
| WO | 2013121162 | A1 | 8/2013 |
| WO | 2013140346 | | 9/2013 |
| WO | 2013141896 | | 9/2013 |
| WO | 2013101292 | A3 | 10/2013 |
| WO | 2014066254 | | 5/2014 |
| WO | 2014066255 | | 5/2014 |
| WO | 2014121162 | | 8/2014 |
| WO | 2014121163 | | 8/2014 |
| WO | 2014121167 | | 8/2014 |
| WO | 2014121169 | | 8/2014 |

OTHER PUBLICATIONS

International Search Report, PCT/US2012/034333 mailed Aug. 29, 2012.
U.S. Appl. No. 60/650,497.
Roberts, The regenerative dialysis (REDY) sorbent system, Nephrology, 1998, 275-278 : 4.
Bleyer, et. al., Sudden and cardiac death rates in hemodialysis patients, Kidney International, 1999, 1553-1559 : 55.
U.S. Appl. No. 61/480,539.
Weiner, et. al., Article: Cardiac Function and Cardiovascular Disease in Chronic Kidney Disease, Book: Primer on Kidney Diseases (Author: Greenberg, et al), 2009, 499-505, 5th Ed., Saunders Elsevier, Philadelphia, PA.
Ronco, et. al., Cardiorenal Syndrome, J. Am. Coll. Cardiol., 2008, 1527-1539 : 52.
Wang, Fundamentals of intrathoracic impedance monitoring in heart failure, Am. J. Cardiology, 2007, 3G-10G : Suppl.
Siegenthalar, et. al., Pulmonary fluid status monitoring with intrathoracic impedance, Journal of Clinical Monitoring and Computing, 2010, 449-451 : 24.
U.S. Appl. No. 13/424,479.
U.S. Appl. No. 13/424,429.
U.S. Appl. No. 13/424,525.
Maclean, et. al., Effects of hindlimb contraction on pressor and muscle interstitial metabolite responses in the cat, J. App. Physiol., 1998, 1583-1592, 85(4).
Overgaard, et. al., Activity-induced recovery of excitability in K+-depressed rat soleous muscle, Am. J: Physiol. Regulatory Integrative Comp. Physiol., 2001, R48-R55, vol. 280.
Overgaard, et. al., Relations between excitability and contractility in rate soleous muscle: role of the NA+-K+ pump and NA+-K+ gradients, Journal of Physiology, 1999, 215-225, 518(1).
U.S. Appl. No. 61/480,541.
U.S. Appl. No. 61/480,535.
U.S. Appl. No. 61/480,530.
U.S. Appl. No. 61/480,528.
ISA Invitation to Pay Additional Fees, PCT/US2012/034323 mailed Aug. 2, 2012.
U.S. Appl. No. 13/757,794, filed Feb. 2, 2013.
U.S. Appl. No. 13/757,722, filed Feb. 1, 2013.
U.S. Appl. No. 13,837,287, filed Mar. 15, 2013.
U.S. Appl. No. 13/757,792, filed Feb. 2, 2013.
U.S. Appl. No. 13/791,755, filed Mar. 8, 2013.
PCT/US2014/014357 International Search Report and Written Opinion.
U.S. Appl. No. 61/480,544.
Wang, Fundamentals of intrathoracic impedance monitoring in heart failure, Am. J. Cardiology, 2007, 3G-310: Suppl.
Brynda, et. al., The detection of toman 2-microglcbuiin by grating coupler immunosensor with three dimensional antibody networks. Biosensors & Bioelectronics, 1999, 363-368, 14(4).
Hemametrics, Crit-Line Hematocrit Accuracy, 2003, 1-5, vol. 1, Tech Note No. 11 (Rev. D).
Lima, et. al., An electrochemical sensor based on nanostructure hollsndite-type manganese oxide for detection of potassium ion, Sensors, 2009, 6613-8625, 9.
Nedelkov, et. al., Design of buffer exchange surfaces and sensor chips for biosensor chip mass spectrometry, Proteomics, 2002, 441-446, 2(4).
PCT/US/2012/034327, International Search Report, Aug. 13, 2013.
PCT/US/2012/034329, International Search Report, Dec. 3, 2012.
PCT/US2012/034331, International Search Report, Jul. 9, 2012.
PCT/US2012/034332, International Search Report, Jul. 5, 2012.
PCT/US2012/034334, International Search Report, Jul. 6, 2012.
PCT/US2012/034335, International Search Report, Sep. 5, 2012.
Redfield, et. al, "Restoration of renal response to atria! natriuretic factor in experimental low-output heat failure", Am. J. Physiol., 1989, R917-923 : 257.
Rogoza, et. al., Validation of A&D UA-767 device for the self-measurement of blood pressure, Blood Pressure Monitoring, 2000, 227-231, 5(4).
Secemsky, et. al, High prevalence of cardiac autonomic dysfunction and T-wave alternans in dialysis patients. Heart Rhythm, Apr. 2011, 592-598 : vol. 8, No. 4.
Wei, et. al., Fullerene-cryptand coated piezoelectric crystal urea sensor based on urease, Analytica Chimica Acta, 2001,77-85:437.
Zhong, et. al., Miniature urea sensor based on H(+)-ion sensitive field effect transistor and its application in clinical analysis, Chin. J. Biotechnol., 1992, 57-65. 8(1).
Leifer, I., et al., A Study on the Temperature Variation of Rise Velocity for Large Clean Bubbles, J. Atmospheric & Oceanic Tech., vol. 17, pp. 1392-1402.
Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
Talaia, Mar, Terminal Velocity of a Bubble Rise in a Liquid Column, Talaia, World Acad. of Sci., Engineering & Tech., vol. 28, pp. 264-268.
The FHN Trial Group. In-Center. Hemodialysis Six Times per Week versus Three Times per Week, New England Journal of Medicine, 2010.
U.S. Appl. No. 13/757,693, filed Feb. 1, 2013.
Coast, et al. 1990, An approach to Cardiac Arrhythmia analysis Using Hidden Markov Models, IEEE Transactions on Biomedical Engineering. 1990, 37 (9):826-835.
PCT/US2012/034330, International Preliminary Report on Patentability, Oct. 29, 2013.
PCT Application, PCT/US20013/020404, filed Jan. 4, 2013.
U.S. Appl. No. 14/261,651, filed Apr. 25, 2014.
U.S. Appl. No. 13/836,973, filed Mar. 15, 2013.
U.S. Appl. No. 14/259,655, filed Apr. 23, 2014.
U.S. Appl. No. 14/259,589, filed Apr. 23, 2014.
PCT/US2012/034333, International Preliminary Report on Patentability, Oct. 29, 2013.
PCT/US2012/034333, International Search Report, Aug. 29, 2013.
U.S. Appl. No. 13/368,225.
U.S. Appl. No. 13/424,533.
U.S. Appl. No. 13/424,467.
U.S. Appl. No. 13/424,454.
U.S. Appl. No. 13/424,490.
U.S. Appl. No. 13/424,517.
U.S. Appl. No. 61/480,532.
U.S. Appl. No. 13/757,794, filed Feb. 2, 2012.
Bleyer, et. al., Sudden and cardiac death rated in hemodialysis patients, Kidney International, 1999, 1553-1559 : 55.
Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
PCT/US2012/034335, International Preliminary Report on Patentability, Nov. 7, 2013.
PCT/US2012/034329, International Preliminary Report on Patentability, Oct. 29, 2013.

(56) References Cited

OTHER PUBLICATIONS

U.S. Appl. No. 13/424,517 IDS, filed Aug. 2, 2012.
U.S. Appl. No. 13/424,517, IDS filed Dec. 2, 2013.
PCT/US2012/034332, Internatonal Preliminary Report on Patentability, Oct. 29, 2013.
PCT/US2012/034303, Internationa Search Report, Jul. 6, 2013.
PCT/US2012/034327, International Preliminary Report on Patentability, Oct. 29, 2013.
Zoccali, Pulmonary Congestion Predicts Cardiac Events and Mortality in ESRD, Clinical Epidemiology, J. Am Soc Nephrol 24:639-646, 2013.
Velasco, Optimal Fluid Control can Normalize Cardiovascular Risk Markers and Limit Left Ventricular Hypertrophy in Thrice Weekly Dialysis Patients, Hemodialysis Intenational, 16:465-472, 2012.
Whitman, CKD and Sudden Cardiac Death: Epidemiology, Mechanisms, and Therapeutic Approaches, J Am Soc Nephrol, 23:1929-1939, 2012.
Hall, Hospitalization for Congestive Heart Failure: United States, 2000-2010, NCHS Data Brief, No. 108, Oct. 2012.
Albert, Fluid Management Strategies in Heart Failure, Critical Care Nurse, 32:20-32, 2012.
PCT/US2014/065201 International Search Report mailed May 26, 2015.
John Wm Agar: "Review: Understnading sorbent dialysis systems," Nephrology, vol. 15, No. 4, Jun. 1, 2010, pp. 406-411.
Office Action in U.S. Appl. No. 13/424,490 Dated Oct. 22, 2013.
Office Action in U.S. Appl. No. 13/424,490 Dated Mar. 10, 2014.
Office Action in U.S. Appl. No. 13/424,490 Dated Jul. 14, 2014.
Office Action in U.S. Appl. No. 13/424,490 Dated Dec. 5, 2014.
Office Action in U.S. Appl. No. 13/424,454 Dated Mar. 10, 2014.
Office Action in U.S. Appl. No. 13/424,454 Dated Oct. 17, 2013.
Office Action in U.S. Appl. No. 13/424,429 Dated Oct. 15, 2015.
Office Action in U.S. Appl. No. 12/571,127 dated Nov. 8, 2012.
Office Action in U.S. Appl. No. 12/571,127 dated Feb. 27, 2014.
Office Action in U.S. Appl. No. 12/571,127 dated Jul. 6, 2015.
Office Action in U.S. Appl. No. 12/571,127 dated Dec. 17, 2015.
Office Action in U.S. Appl. No. 13/424,467 Dated Oct. 16, 2013.
Office Action in U.S. Appl. No. 13/424,467 Dated Mar. 3, 2014.
Office Action in U.S. Appl. No. 14/554,338 Dated Jun. 7, 2016.
Office Action in U.S. Appl. No. 14/554,338 Dated Sep. 28, 2016.
Office Action in U.S. Appl. No. 14/554,272 Dated Aug. 8, 2016.
Office Action in U.S. Appl. No. 13/424,479 Dated Oct. 25, 2014.
Office Action in U.S. Appl. No. 13/757,792 Dated Apr. 6, 2015.
Office Action in U.S. Appl. No. 14/566,686 Dated Apr. 28, 2016.

* cited by examiner

CHRONIC PH OR ELECTROLYTE MONITORING

RELATED APPLICATION

This application claims priority to U.S. Provisional Application No. 61/480,539, U.S. Provisional Application No. 61/480,544, U.S. Provisional Application No. 61/480,541, U.S. Provisional Application No. 61/480,535, U.S. Provisional Application No. 61/480,532, U.S. Provisional Application No. 61/480,530, and U.S. Provisional Application No. 61/480,528, wherein each priority application was filed Apr. 29, 2011, wherein each priority application is hereby incorporated by reference in its entirety to the extent that it does not conflict with the disclosure presented herein.

FIELD

The present disclosure relates generally to devices, systems and methods for monitoring electrolytes or pH in patients for which blood cleaning or fluid removal is indicated, such as patients suffering from kidney disease or heart failure.

BACKGROUND

Patients who undergo hemodialysis or other procedures that remove solutes and fluid from the blood often die of cardiac complications. Many factors may contribute to such death, including stress placed on the heart due to the increased blood fluid volume in these patients. Increased fluid concentrations and inability to remove waste products from the blood, in some cases, can also contribute to electrolyte and pH imbalance that can affect cardiac contractility and efficiency. Further, rapid changes in fluid volume or pH or electrolyte concentration of the blood during hemodialysis or other fluid removal processes may place additional stress on the heart and may contribute to the high rate of morbidity for patients who undergo blood fluid removal procedures.

When a patient reaches a point where routine blood fluid removal procedures are prescribed, the patient undergoes periodic examinations that allow a healthcare provider to set various parameters of the blood fluid removal procedures, such as the profile of fluid removal, the composition of dialysate or replacement fluid employed, and the like. These examinations typically occur once a month in accordance with current standards of care.

Hemodialysis or similar procedures may occur three to four times a week. Thus, the patient may undergo 10 to 15 or more blood fluid removal sessions before the prescription or parameters are changed. It is possible, for example, that a prescription with regard to a dialysate electrolyte and pH buffer composition will not be appropriate for a patient several days or weeks after the prescription is set. Accordingly, it may be desirable to more frequently determine whether the electrolyte or pH concentration of a fluid used in blood fluid removal sessions is appropriate. In addition, it may be desirable to adjust the concentration or composition of the fluid during a blood fluid removal session in a manner that may improve patient health and reduce morbidity.

SUMMARY

This disclosure, among other things, describes devices, systems and methods for monitoring pH or electrolytes in patients for which blood fluid removal sessions are indicated. The monitoring may occur prior to a blood fluid removal session, and data acquired from the monitoring may be used to assist in determining an appropriate initial concentration and composition of buffer (pH) or electrolytes for use during the session. Alternatively, or in addition, the monitoring may occur during a blood fluid removal session, and the concentration or composition of buffer or electrolytes may be adjusted based on monitored data acquired during the blood fluid removal session. By monitoring pH or electrolytes, a more appropriate initial dialysate or replacement fluid may be used, or the fluid may be adjusted during a session, to enhance patient safety.

In various embodiments described herein, a method includes identifying a patient for which a blood fluid removal session is indicated and monitoring an indicator of blood electrolyte concentration or blood pH of the patient. The method may further include determining whether the monitored indicator crosses a predetermined threshold, and alerting the patient or healthcare provider, or automatically scheduling a blood fluid removal session, if the indicator is determined to cross the threshold. In various embodiments, the method includes determining an appropriate electrolyte concentration or buffer concentration for a fluid to be used in a blood fluid removal session based on the monitored indicator.

In some embodiments, a method includes initiating a blood fluid removal procedure for a patient in need thereof. The procedure includes use of a fluid selected from a dialysate fluid or a replacement fluid. The fluid has an initial pH buffer composition or electrolyte composition. The method further includes monitoring an indicator of blood electrolyte concentration or blood pH of the patient during the blood fluid removal session, via an implantable or wearable sensor, and adjusting the pH buffer composition or the electrolyte composition of the fluid based on a value of the monitored indicator.

In embodiments, a system includes a blood fluid removal device, which has (i) an inlet for receiving blood from a patient, (ii) an outlet for returning blood from the patient, (iii) a medium for removing fluid and contaminants from the blood, the medium being positioned between the inlet and the first outlet, and (iv) a fluid source for carrying a fluid, where the fluid is selected from dialysate and replacement fluid. If the fluid is dialysate, the fluid source carries the fluid to the medium. If the fluid is replacement fluid, the fluid source carries the fluid to the blood after the blood exits the medium. The system further includes (i) a concentrate source for housing a concentrate solution comprising concentrated electrolyte or pH buffer, (ii) a concentrate flow control element for controlling the rate that the concentrate solution enters the fluid source; (iii) an implantable sensor for monitoring an indicator of blood pH or blood electrolyte concentration; and (iv) control electronics in operable communication with the sensor and the concentrate flow control element. The control electronics are configured, via the concentrate flow control element, to adjust the rate at which the concentrate solution enters the fluid source based on data obtained from the sensor.

One or more embodiments of the systems, devices and methods described herein may provide one or more advantages over prior systems, devices and methods for blood fluid removal in patients. Such advantages will be apparent to those skilled in the art upon reading the following detailed description.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

FIG. 7; open loop: FIG. 8) for controlling flow of concentrate into fluid for use in a blood fluid removal process based on monitored pH or electrolytes.

Figure 1:
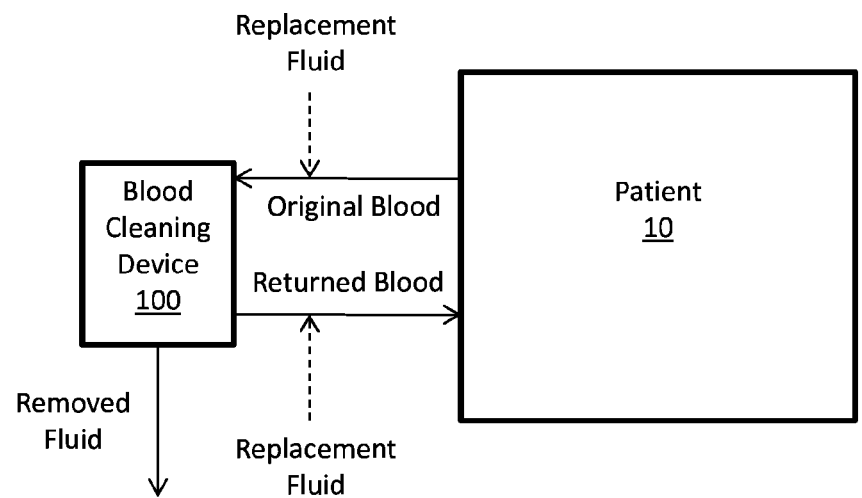
FIGS. 1-3 are schematic block diagrams showing interaction of blood fluid removal devices with a patient showing flow of blood (dashed arrows) and fluid (solid arrows), which blood fluid removal devices may be used in various embodiments described herein.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

As used herein, a "patient for which a blood fluid removal session is indicated" is a patient that has undergone, is undergoing, or is likely to undergo at least one blood fluid removal session. In general, such patients are fluid overloaded patients, such as patients suffering from heart failure, chronic kidney disease, or acute kidney failure. Often such patients are stage 3 to stage 5 chronic kidney disease patients, are unresponsive or under-responsive to diuretics, or the like.

As used herein, a "blood fluid removal process," or the like, refers to a process from which fluid is removed from blood of a patient and the blood is returned to the patient. In most (if not all) cases, blood fluid removal processes result in removal of waste products from the blood, and cleaned blood is returned to the patient. Examples of such processes include ultrafiltration, hemofiltration, hemodialysis, hemodiafiltration, peritoneal dialysis and the like. Any patient for which blood fluid removal is indicated may benefit from the devices, systems and methods described herein.

This disclosure relates to, among other things, systems and methods for monitoring pH or electrolyte concentrations in patients for which a blood fluid removal process is indicated. Sensors are used to monitor pH and electrolytes in the patient. In embodiments, the sensors monitor pH, electrolytes, or indicators thereof, in the patient's blood. In embodiments, the sensors monitor pH or electrolytes, or indicators thereof, in tissue or fluid other than the blood. Other tissues or fluids tend to equilibrate with blood. Accordingly, changes in pH or electrolyte levels in tissue or fluid other than blood may be indicative of changes of pH or electrolytes in blood. Of course, there may be some delay in the relative time of changes in pH or electrolytes in tissue or fluid other than blood relative to changes in blood, which delay may be accounted for. In addition to absolute values of monitored indicators, trends showing downward or upward changes in pH or electrolytes in tissue or fluid other than blood may be correlated to changes in blood pH or blood electrolytes. In embodiments, sensors are placed to detect pH or electrolytes in, for example, a peritoneal cavity or a cerebrospinal fluid compartment of the patient.

In some embodiments, an initial buffer or electrolyte concentration or composition of a fluid for use in the blood fluid removal process may be selected based on data acquired from the sensors. Any suitable device or system for removing fluid, or fluid and contaminants, from blood may be used in accordance with the teachings presented herein. The devices, or components thereof, may be traditional large counsel-type, wearable, or implantable.

Figure 2:
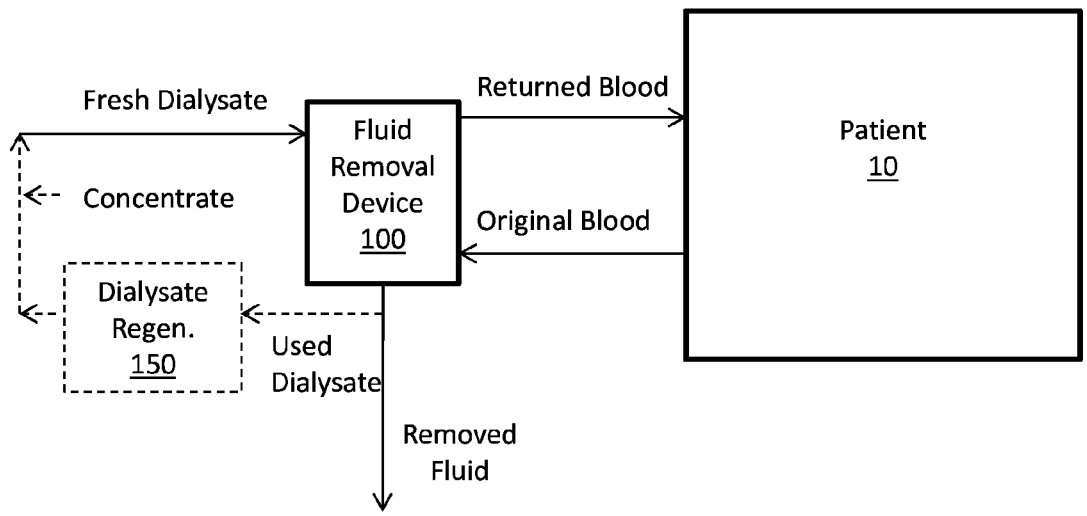
Figure 3:
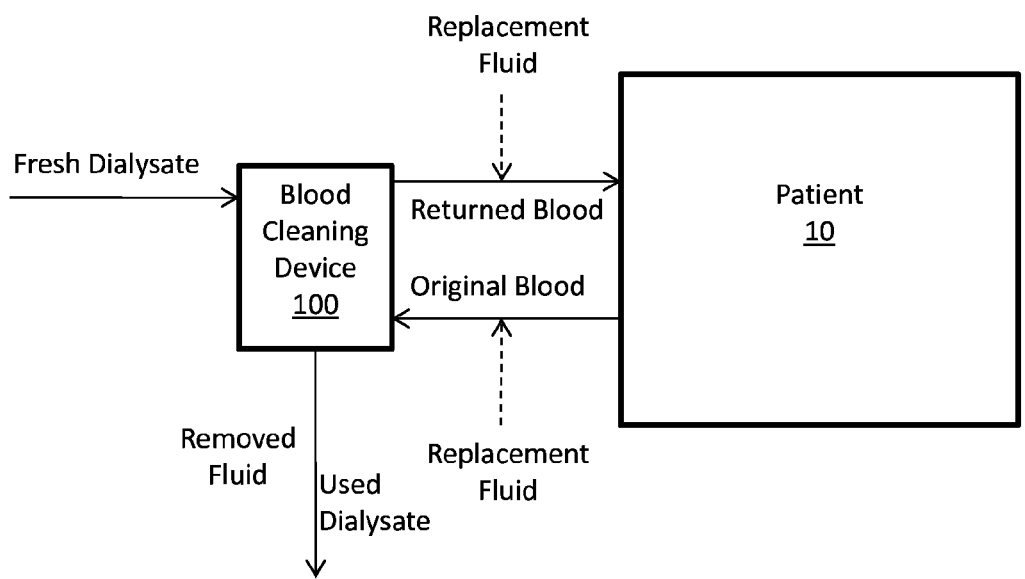

Block diagrams of some example devices and systems are shown in FIGS. 1-3. As shown in FIG. 1, blood may be removed from a patient 10 and fluid may be removed via a blood fluid removal device 100 and returned to the patient 10. Removed fluid may be diverted. In some embodiments where the blood fluid removal device 100 or system, or components thereof, are implanted, the removed fluid may be diverted to the patient's bladder. Examples of blood fluid removal devices 100 that may operate as depicted in FIG. 1 are ultrafiltration and hemofiltration devices. Examples of such devices and components thereof that may be employed in accordance with the teachings presented herein are well known in the art. With some of such devices, replacement fluid may be introduced into the patient's blood if fluid is removed from the blood by the device 100 at too great of a rate or amount. The replacement fluid may be added to the original blood before fluid removal or may be added to the blood after initial fluid removal and prior to return to the patient's cardiovascular system. Preferably, the replacement fluid is added after initial fluid removal. The pH and electrolyte concentration of the replacement fluid may be set or adjusted, e.g. as described in more detail below, based on monitoring of pH or electrolytes of the patient.

As shown in the embodiment depicted in FIG. 2, the blood fluid removal device 100 may employ dialysate to assist in removal of contaminants from the patient's blood and in maintaining proper pH and electrolyte balance. The pH or electrolyte concentration of the dialysate may be set or adjusted, e.g. as described in more detail below, based on monitoring of pH or electrolytes. Used dialysate and fluid removed from the blood may be diverted. In some embodiments, particularly where the blood fluid removal device 100 or system or components thereof are wearable or implantable, the used dialysate and removed fluid, or a portion thereof, may be regenerated (indicated by dashed lined regeneration system 150) to produce fresh dialysate for re-use in the blood fluid removal process. One system for regeneration of dialysate is the REDY system, such as described in Roberts, M, "The regenerative dialysis (REDY) sorbent system," *Nephrology* 4:275-278, 1998, which system may be employed or readily modified for use in embodiments described herein. As shown in FIG. 2, a concentrate may be added to the regenerated dialysate to adjust the pH and electrolytes of the regenerated dialysate to an amount suitable for re-use as fresh dialysate.

Regardless of whether the dialysate is regenerated, systems and devices that operate in a manner shown in the embodiment of FIG. 2 include hemodialysis and hemodiafiltration systems. Examples of such devices and components thereof that may be employed in accordance with the teachings presented herein are well known in the art. It will be understood that peritoneal dialysis, where the dialysate is introduced into the peritoneal cavity may also be employed.

As shown in FIG. 3, in cases where the blood fluid removal device 100 of FIG. 2 removes fluid from the blood at too high of a rate, replacement fluid may be introduced into the patient's blood, upstream or downstream of fluid removal, e.g. as described above with regard to FIG. 1.

Regardless of the device or blood fluid removal process employed, it is important to ensure that the blood pH and electrolyte concentrations are within suitable ranges. If blood electrolyte concentrations are not within suitable ranges, problems with cardiac contractility, efficiency and the like may occur. If the pH is not within a suitable range, acidosis may result, which can result in disruption of cell membranes and denaturation of proteins. In either case, if ranges of blood electrolytes and pH are not properly controlled, the patient's health may be at risk. For example, sudden and cardiac death (including death from congestive heart failure, myocardial infarction, and sudden death) are common in hemodialysis patients. See Bleyer et al, "Sudden and cardiac death rated in hemodialysis patients," *Kidney International*, (1999), 55:1552-1559.

Accordingly, one goal of hemodialysis, ultrafiltration, and the like is to ensure that the patient's blood pH and electrolyte concentrations are within acceptable ranges. Typical ranges of pH and blood electrolyte concentration that are desired during or following a blood fluid removal session are provided in Table 1 below. As indicated in Table 1, concentrations of various acids or bases (or salts or hydrates thereof) are often important in determining the pH of blood. Accordingly, some typical target concentrations of such acids or bases are presented in Table 1.

TABLE 1

Typical target ranges for pH and electrolytes
(ref. Medical Surgical Nursing, 7$^{th}$ Ed., 2007)

|  | Target Range |
| --- | --- |
| pH | 7.35-7.45 |
| Phosphate | 2.8-4.5 mg/dL |
| Bicarbonate | 22-26 mEq/L |
| Cl$^-$ | 96-106 mEq/L |
| Mg$^{2+}$ | 1.5-2.5 mEq/L |
| Na$^+$ | 135-145 mEq/L |
| K$^+$ | 3.5-5.0 mEq/L |
| Ca$^{2+}$ | 4.5-5.5 mEq/L |

However, it will be understood that the target for a particular patient may be different from the values presented in Table 1 for one or more electrolyte or pH. It will also be understood that buffers are typically employed to maintain proper blood pH.

Some suitable buffers that may be used in fluid, such as replacement fluid or dialysate, include bicarbonate, acetate, lactate, citrate, amino acid and protein buffers. The concentration and composition of the buffers and components thereof may be adjusted based on monitored pH of the patient's blood. Similarly, the concentration of electrolytes such as sodium, potassium, calcium, and chloride in replacement fluid or dialysate may be set or altered based the monitored levels of electrolytes.

The methods, systems and devices described herein may be used, in some embodiments, to set the initial electrolyte concentration and pH (buffer components and concentration) based on monitoring that occurs before a blood fluid removal session starts. In some embodiments, the monitoring is chronic; e.g., monitoring is performed intermittently, periodically or continuously over the course of days, weeks, months or years. In an attempt to minimize interference with the patient's lifestyle, the monitoring system, or components thereof, may be implantable or wearable.

Figure 4:
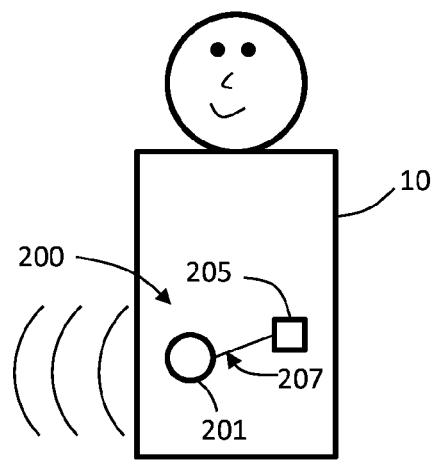
FIG. 4 is a schematic diagram of an embodiment of a sensor device implanted in a patient.
Figure 5:
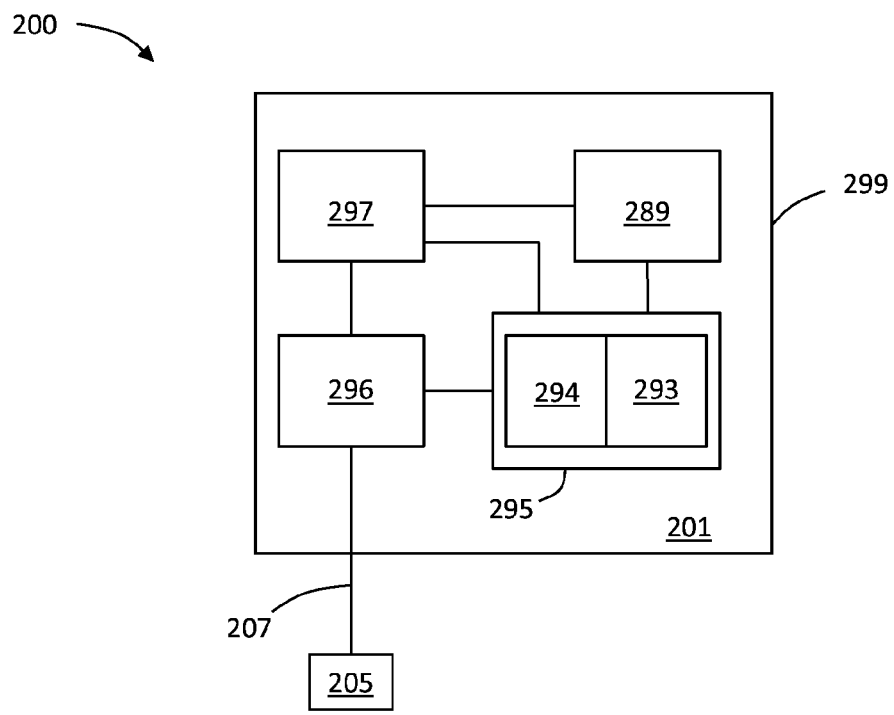
FIG. 5 is a schematic block diagram showing some selected components of an embodiment of a sensor device.
Figure 6:
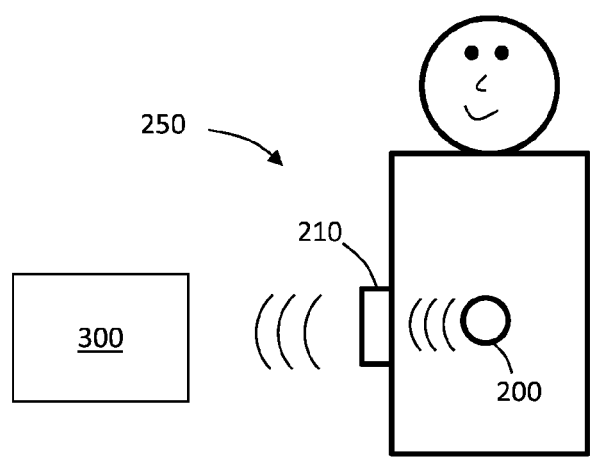
FIG. 6 is a schematic diagram of an embodiment of a implanted sensor device configured to communicate with an external device, which is configured to communicate with a remote device.

For example and with reference to FIGS. 4-6, embodiments of monitoring devices or systems that have implantable or wearable components are shown. In the embodiment depicted in FIG. 4, sensor device 200 is fully implantable in the patient 10 and is capable of communicating with devices outside of the patient or other implanted devices via telemetry or other suitable form of communication. The sensor 200 includes a device body 201 containing electronic components within a hermetically sealed housing. A transducer 205 is operably coupled to the electronics of the device body 201 via a lead 207. In this manner the device body 201 may be implanted at a location removed from the sensor or transducer 205. In some embodiments, the sensor 200 is leadless, and the transducer is incorporated into the device body 210 or a portion thereof, such as a portion of the housing.

The transducer 205, whether in a leadless or lead-containing device 200, may be placed within a blood vessel so that measurements of blood pH or blood electrolyte concentrations can be determined. The transducer 205, or device body 201 (if leadless), may be placed in any suitable blood vessel to monitor pH or electrolytes, or indicators thereof. In some embodiments, the transducer 205, or device body 201 (if leadless), is placed in a femoral artery or a pulmonary artery. An example of a leadless implantable monitor for placement in a blood vessel is Medtronic, Inc.'s active leadless pressure sensor (ALPS), which generally takes the form of a stent to anchor the device within vessel. It is understood that the ALPS sensor device may be modified for purpose of monitoring pH or electrolyte concentrations.

In embodiments, the transducer is placed in tissue or fluid other than blood of the patient. Measurements of ion concentration may be correlated to blood electrolyte concentration or blood pH.

Any suitable transducer 205 may be employed to detect pH or electrolytes, regardless of where the transducer 205 is placed. In embodiments, the transducer 205 is an ion selective electrode configured to detect $H^+$ ions, $K^+$ ions, $Na^+$ ions, $Ca^{2+}$ ions, $Cl^-$ ions, phosphate ions, magnesium ions, acetate ions, amino acids ions, or the like. Such electrodes, and components of sensors employing such electrodes, are known in the art and may be employed, or modified to be employed, for use in the monitoring described herein.

In some embodiments, one or more sensors are employed to detect one or more ions to gauge pH or electrolytes in the blood. In some embodiments, a sensor may have more than one transducer, even if leadless, that may monitor more than one ionic species. By measuring more than one ionic species, a more detailed understanding of the levels of various electrolytes or blood components may be had. For example, in some patients in some situations, one electrolyte may be at elevated levels while another may be at reduced levels. In some embodiments, more than one sensor for the same ion is employed for purposes of result confirmation and redundancy, which can improve reliability and accuracy. In some embodiments, sensors for the same ion may be configured to accurately detect different ranges of concentrations of the ion. In embodiments, more than one transducer is present in a single unit. This allows for convenient data collection and circuitry, as all the data may be collected in one place at the same time. Further, the multiple transducers may share the same fluid collection mechanism (e.g., a microdialyzer in the case of an implant), and if needed or desired, may share the same data processing and memory storage components.

Implantable sensors or sensors in which the transducer is chronically inserted in a tissue or blood of a patient may be calibrated prior to implant by placement of the transducer in blood (or other conditions mimicking the implant environment) with known pH or electrolyte concentrations. The sensors 200 may be recalibrated while implanted in the patients. For example, blood pH and electrolyte concentration can be measured external to the patient, e.g., via blood draws, and results of the external monitoring can be communicated to the implanted sensor 200 by receiving input, e.g., from healthcare providers. Thus, the sensor 200, if sensor has necessary electronics (e.g., as discussed below in more detail), can recalibrate based on the input regarding the external measurements. Alternatively, or in addition, the sensor may have an internal reference built in, such as with the Medtronic, Inc. Bravo® pH sensor. Alternatively, in cases where the sensor outputs raw data to an external device, the external device may be calibrated to interpret the raw data from the sensor with regard to input regarding the external measurements.

For purposes of illustration, a block diagram of a generic implantable sensing device 200 (e.g., as depicted in FIG. 4) is shown in FIG. 5. The depicted sensor is implantable and has a hermetically sealed housing 299 for containing various electronic components 296, 297, 289, 295. Sensing circuitry 296, such as analog-to-digital convertor, band-pass filter, or the like, is operably coupled to power supply 297 and control electronics 295, which include a processor 294 and a memory 293 for storing sensed data and processor instructions. Sensing circuitry 296 is also operably coupled to transducer 205, such as an ion selective electrode, via lead 207, which enters housing 299 via a hermetic feedthrough (not shown). Control electronics 295 are also operably coupled to power supply 297, which may be a battery or the like, and to telemetry circuitry 289 for wirelessly communicating with a device external to the patent or with another device implanted in the patient. In some embodiments, the telemetry circuitry 289 allows the sensor device 200 to transmit data regarding a monitored pH or electrolyte directly to a blood fluid removal device or system that is equipped with suitable telemetry circuitry.

Referring now to FIG. 6, an embodiment of a sensor system 250, in which the implanted sensor device 200 (leadless is shown, but may include lead as depicted in FIG. 4), communicates with an external device 210. The external device 210 may be worn and may carry out some processing of data acquired by sensor 200 to reduce power consumption of implanted sensor 200, for purpose of size, computing power, upgradeability, or the like. Any suitable external device 210, such as a computer, personal data assistant, smart phone, patient programmer device, or the like, may be employed. In embodiments, the external device 210 communicates with remote device 300. Of course, in some embodiments, the implanted sensor 200 may communicate directly with remote device 300.

Remote devices 300 may be devices associated with blood fluid removal, and data transmitted by external device 210 may be used to set or adjust fluid pH and electrolyte concentrations before or during a blood fluid removal session. Remote device 300 may be a computer, personal data assistant or the like connected to the internet or a phone network, allowing sensed data or other information regarding sensed data to be transmitted to a healthcare provider. For example, the sensed data, or information regarding the sensed data, may be used to prepare an appropriate initial fluid (e.g., dialysate or replacement fluid) for use in the patient's next blood fluid removal session. If the monitored pH or electrolytes are out of a predetermined range, an appointment to see a healthcare provider or to schedule a blood fluid removal session may be performed automatically. In some embodiments, remote device 300 is a physician programmer device. Of course, remote device 300 may be any other suitable device.

In various embodiments, data acquired from blood pH or electrolyte sensors may be used to adjust the pH of electrolytes of fluid (e.g., dialysate or replacement fluid, see, e.g., FIGS. 1-3) during a blood fluid removal session, as long as the blood fluid replacement device or system is equipped to adjust the concentration of such components. Some examples of such devices that may be used, or modified for use herein, are described in U.S. Provisional Patent Application No. 61/480,532, filed on Apr. 29, 2011, entitled ELECTROLYTE AND pH MONITORING FOR FLUID REMOVAL PROCESSES, which application is incorporated herein by reference in its entirety to the extent that it does not conflict with the present disclosure. The implantable or wearable sensors described herein, e.g. with regard to FIGS. 4-6, may be used as sensors that monitor an indicator of blood pH or blood electrolyte concentration before the blood enters a blood fluid removal device or media in accordance with the incorporated provisional application.

The pH or electrolyte sensors, e.g. as described above, may be employed to understand how to appropriately adjust the pH or electrolyte level. Data acquired from the sensors may be transmitted to blood fluid removal devices or devices in communication with blood fluid removal devices (such as devices depicted in FIGS. 1-3 and described above) for adjusting the concentration of pH buffers or electrolytes in dialysate or replacement fluid. The pH and electrolyte concentration of the fluid (dialysate or replacement fluid) may be adjusted in any suitable manner.

Figure 7:
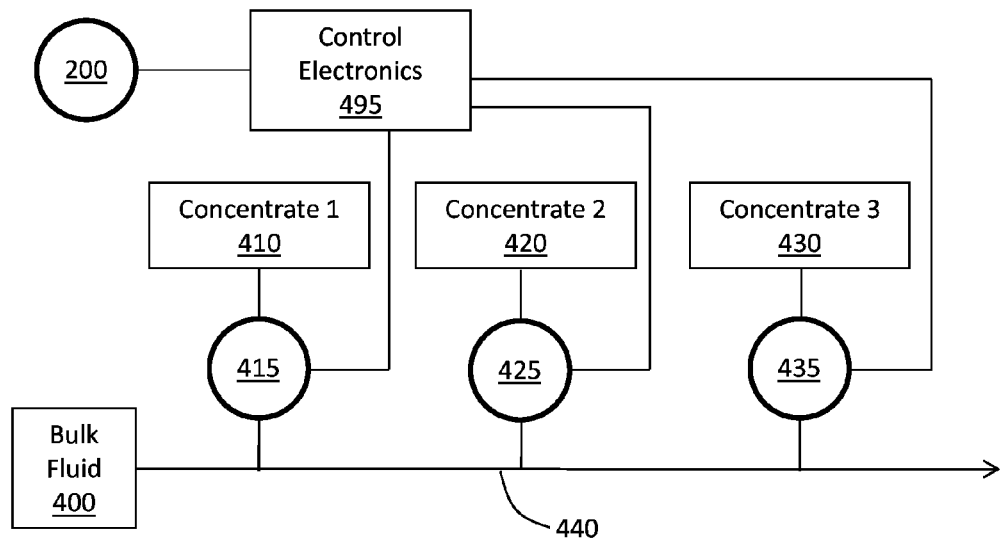
FIGS. 7-8 are schematic block diagrams showing flow paths and some control mechanisms (closed loop.
Figure 8:
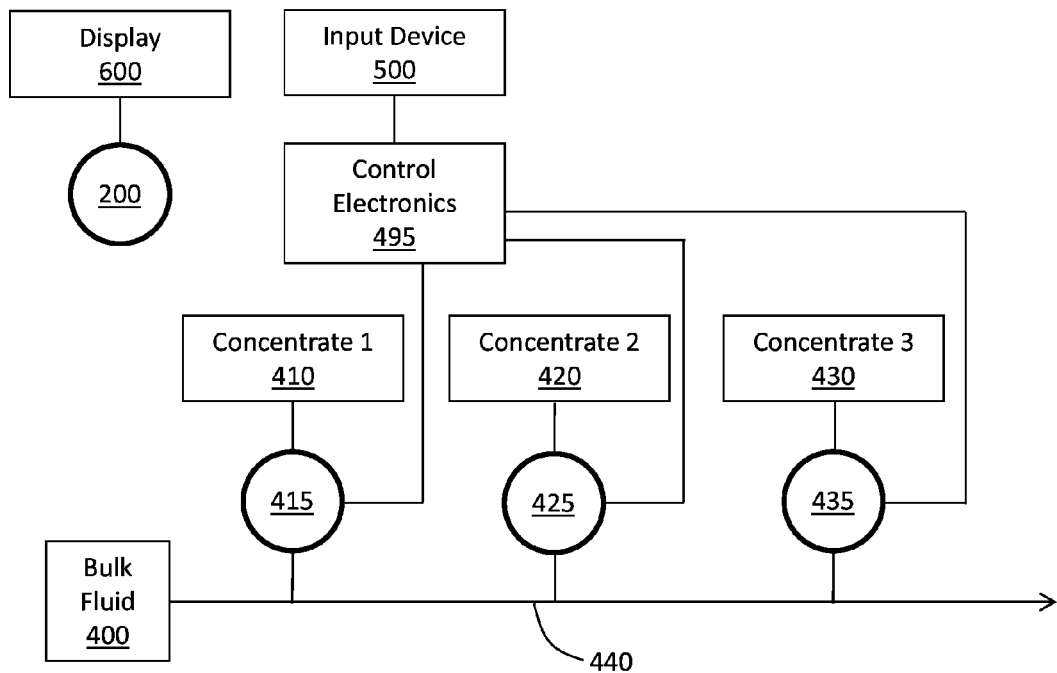

For example and with reference to FIGS. 7-8, some representative components of an example of a closed-loop system (FIG. 7) and an open-loop system (FIG. 8) for adjusting pH and electrolyte concentrations of fluid are shown. With reference to FIG. 7, data from sensor 200 (e.g., as described above with regard to FIGS. 4-6) is presented to control electronics 495, which are configured to control flow control elements 415, 425, 435, such as valves. The electronically controllable flow control elements 415, 425, 435 are in fluid communication with supplies of concentrated electrolyte or buffer solutions 410, 420, 430 and with fluid line 440, which may be a catheter for carrying fresh dialysate or a catheter for carrying replacement fluid. The electronically controllable flow control elements 415, 425, 435, via control electronics 495, control the rate at which the concentrates 410, 420, 430 flow into the fluid line 440. The concentrates 410, 420, 430 are added to bulk fluid 400 to adjust the concentration of electrolytes or the pH of the bulk fluid (and thus the blood).

Referring now to FIG. 8, data from sensor 200 may be processed and appropriate information presented on a display 600, which may be a part of the blood fluid removal device, a separate computer, or the like. A healthcare provider may use the information presented on the display 600 to adjust the concentration of electrolytes or pH. This can be done, for example, by transmitting appropriate instructions to the control electronics via an input device 500. Any suitable input device 500 may be used. For example, input device 500 may be a keyboard, a computer, a tablet, a personal data assistant, a physician programmer, or the like. In some embodiments, the input device 500 is the display 600; e.g., where the display 600 is a touch screen device. Regardless of how the instructions are input, the control electronics 495 can control flow control elements 415, 425, 435 to control the amount of concentrate 410, 420, 430 introduced to bulk fluid 400, which may be dialysate or replacement fluid.

Any number of suitable concentrates may be used. For example, one concentrate may be sufficient with higher amounts being added when the electrolytes are determined to be low in the patient's blood, and smaller amounts being added when the electrolytes are determined to be high in the patient's blood. More than one concentrate may be used when it is desired to, for example, control pH and electrolyte concentration independently or to control concentration of different electrolytes independently. In embodiments, the number of concentrates is the same as the number of ion species (pH and electrolytes) monitored.

Control elements 415, 425, 435, as depicted in, and described with regard to, FIGS. 7-8, may be any suitable control element, such as electronically controllable valves, electronically controllable pump mechanisms, or the like.

Control electronics 495, as depicted in, and described with regard to, FIGS. 7-8, may include, for example, a processor and memory. The memory, which may be RAM, ROM, or the like, may store instructions, and the processor may carry out the instructions.

Any suitable system may be configured as depicted in FIGS. 7-8 to provide control of adjustment of pH or electrolytes based on data acquired from one or more sensors. Examples of such systems that may be used, or modified for use herein, are described in U.S. Provisional Patent Application No. 61/480,532, filed on Apr. 29, 2011, entitled ELECTROLYTE AND pH MONITORING FOR FLUID REMOVAL PROCESSES.

While FIGS. 7-8 show devices that can adjust blood electrolyte or pH by adjusting the pH or electrolyte concentration of replacement fluid or dialysate, it will be understood that pH and concentration can also be adjusted by, for example, adjusting the rate at which dialysate or blood is passed over a dialysis membrane. The rate of transfer between blood and dialysate of electrolytes, etc. across the membrane will be dependent on the flow rate of the blood and the dialysate. Accordingly, in systems where dialysate electrolyte concentration or pH cannot be readily adjusted, the rate of flow of blood or dialysate flow may be altered to achieve similar effects to adjusting the concentration of electrolytes in dialysate.

It will be understood that the blood fluid removal devices and systems, and components thereof, described herein are presented for purposes of illustration and not limitation. Components, devices and systems other than those described herein, or derivations of the components, devices and systems described herein, may be employed. Further, it will be understood that, while many of the blood fluid removal devices depicted in a variety of the figures, such as FIGS. 1-3 are shown as external to the patient, the teachings presented herein apply if the device or components thereof, were implanted in the patient.

The devices and systems described above, or components thereof, may be used to carry out the methods depicted in FIGS. 9-13 and described below, or portions thereof. Of course, any suitable device or system may be employed to carry out the methods, or portions thereof, described below. It will be understood that various steps of the methods presented with regard to any one of FIGS. 9-13 below may be interchanged, substituted, or added to steps presented with regard to any other of FIGS. 9-13.

Figure 9:
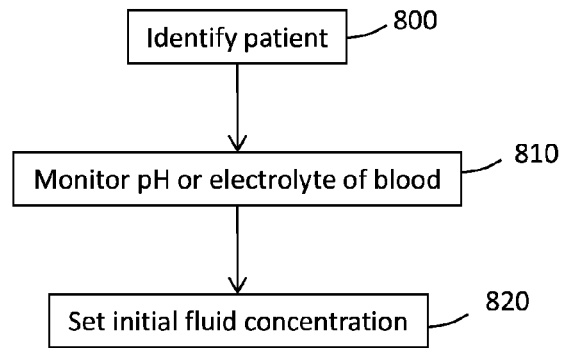
FIGS. 9-13 are flow diagrams illustrating overviews of general methods in accordance with embodiments described herein.
Figure 10:
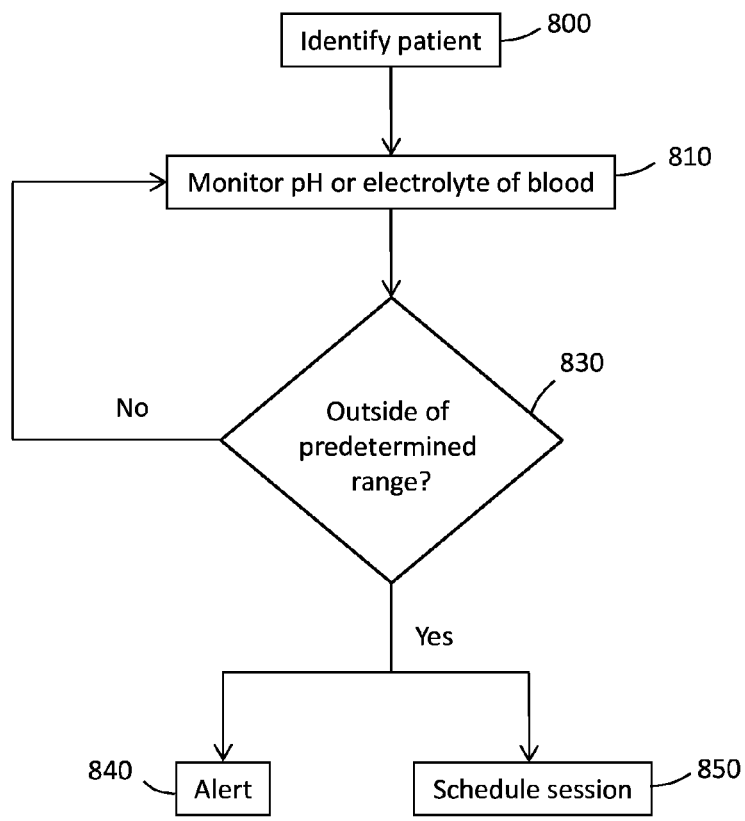
Figure 11:
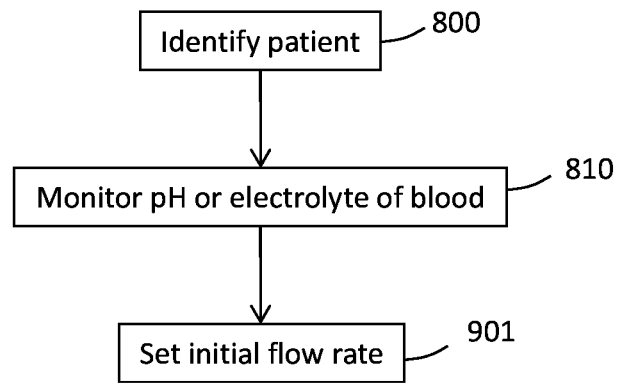
Figure 12:
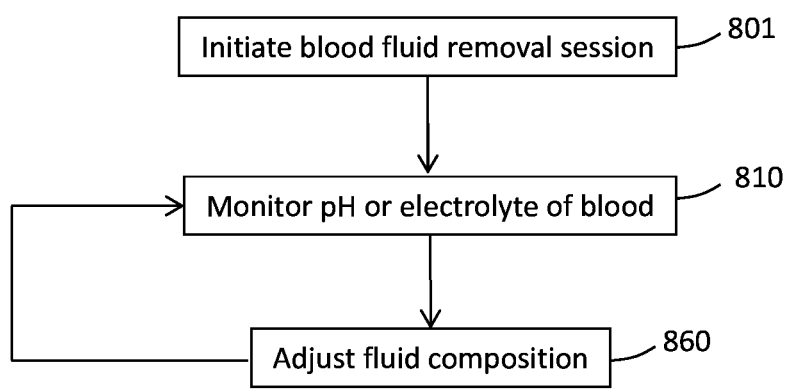
Figure 13:
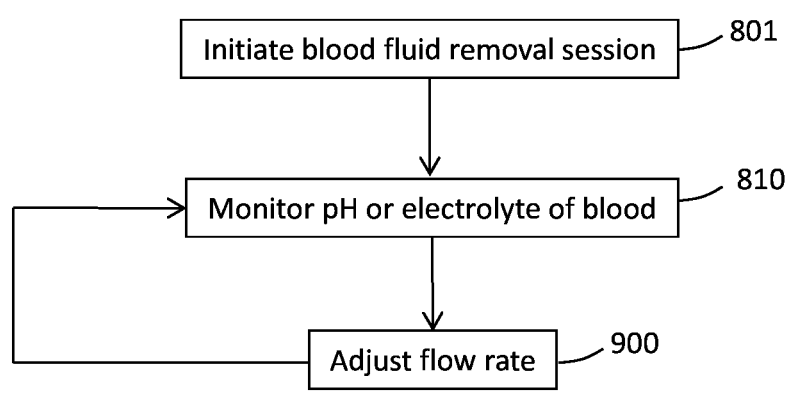

FIGS. 9-11 present embodiments where monitoring is employed prior to a given blood fluid session, and FIGS. 12-13 present embodiments where monitoring is employed during a blood fluid removal session. However, aspects of the methods of FIGS. 9-11 may be incorporated into the methods of FIGS. 12-13.

Referring now to FIG. 9, the depicted method includes identifying, selecting or diagnosing a patient for which a blood fluid removal session is indicated (800) and monitoring pH or electrolyte levels of the blood of the patient (810). The monitoring (810) may be chronic and may employ one or more implantable sensors. Based on the monitored pH or electrolyte concentration, the fluid (e.g., dialysate or replacement fluid) composition (e.g., electrolyte concentration, buffer composition and concentration) for use initial use in a blood fluid removal session may be set (820). As described above, the ability to chronically monitor pH or electrolyte concentrations of the patient's blood provides the ability to tailor the fluid composition prior to each blood fluid removal session, as opposed to current standard practice in which the fluid composition is adjusted on a monthly basis (or thereabout). As multiple blood fluid removal sessions (e.g., two to three a week) may occur with a month, setting the fluid composition on a monthly basis may result in the patient undergoing several blood fluid removal sessions with a fluid composition that may no longer be well suited for the patient.

Referring now to FIG. 10, method includes identifying, selecting or diagnosing a patient for which a blood fluid removal session is indicated (800) and monitoring pH or electrolyte levels of the blood of the patient (810). As with the method in FIG. 9, the monitoring (810) may be chronic and may employ one or more implantable sensors. The method depicted in FIG. 10 includes determining whether the pH or electrolyte concentration is out of range (830) based on data acquired during the monitoring (810). For example, a determination (830) may be made as to whether pH or electrolyte levels crossed a threshold (e.g., a ceiling or floor). Suitable thresholds or ranges may be stored in, for example, a look-up table in memory of a sensor device, a blood fluid removal device, or other suitable device for purposes of determining whether the pH or electrolyte concentration is out of range (830) based on data acquired during the monitoring. If the pH or electrolytes are determined to be within range, monitoring (810) may continue. If the pH or electrolytes are determined to be out of range (e.g., cross a threshold), an alert (840) may be issued or a blood fluid removal session (850) may be scheduled.

The scheduled blood fluid removal session may take into account the monitored (810) pH or electrolytes, e.g. as described with regard to FIG. 9. The scheduling may occur automatically, e.g. the sensor or a device in communication with the sensor may transmit data and cause scheduling of session over internet, telephone, or other suitable network.

Any suitable alert (840) may be issued. The alert may be a tactile cue, such as vibration or audible alarm, generated by a sensor or a device in communication with sensor. The alert may provide the patient with notice that medical attention should be sought. The alert may also provide information to a healthcare provider regarding the nature of the health issue (e.g., pH or electrolytes out of range) and treatment (e.g., blood fluid removal session) for which the alert (840) was issued. The sensor or a device in communication with the sensor may alert the healthcare provider by transmitting the alert or related information over the internet, a telephone network, or other suitable network to a device in communication with the healthcare provider.

Referring now to FIG. 11, the depicted method includes identifying, selecting or diagnosing a patient for which a blood fluid removal session is indicated (800) and monitoring pH or electrolyte levels of the blood of the patient (810). The monitoring (810) may be chronic and may employ one or more implantable sensors. Based on the monitored pH or electrolyte concentration, the rate of flow of dialysate or blood, based in part on the concentration of electrolytes and pH composition of the dialysate, is set (901). As described above, the rate of flow of dialysate or blood affects the rate of transfer of electrolytes, etc. across the dialysis membrane. Accordingly, depending on the composition of the dialysate used, the rate of flow of the dialysate or blood may be adjusted or set so that desirable blood pH and electrolyte levels may be achieved during the course of a treatment session.

Referring now to FIG. 12, the depicted method includes initiating a blood fluid removal session (801) and monitoring pH or electrolyte concentration of blood (810). As discussed above, the monitoring may occur via one or more implanted sensors. Based on the monitored pH or electrolytes, the pH or electrolyte composition or concentration of fluid (e.g., dialysate or replacement fluid) used in the blood fluid removal session may be adjusted (860). For example, based one or more of the current value of a monitored ionic species or the rate of change in the monitored ionic species, the fluid composition may be adjusted, e.g. as discussed above.

Referring now to FIG. 13, the depicted method show a method where blood electrolyte concentration or pH is adjusted by altering the flow rate of dialysate or blood. The method includes initiating a blood fluid removal session (801), such as a hemodialysis session, and monitoring an indicator of pH or electrolyte (810), which can be in the patient, upstream of the device, downstream of the device, within the device, or the like. Based on the monitored data (810), adjustments to the flow of dialysate or blood may be made (900) to adjust the electrolyte concentration or pH in the blood that gets returned to the patient.

The methods described herein, including the methods depicted in FIGS. 9-12, may be carried out by sensor devices, blood fluid removal devices, or other devices in communication with sensor devices or blood fluid removal devices. These methods may be algorithms or instructions programmed into memory of such devices, which may be carried out by processors or other control electronics of the devices. Preferably, the processor is in communication with appropriate control elements of the devices and is configured to control such elements in a manner such that the programmed instructions are carried out by the appropriate device. It will be understood that a computer readable medium programmed with instructions that cause a sensor device, blood fluid removal device, or other suitable device to carry out a method, or a portion thereof, as described herein are contemplated. The computer readable medium may be non-transitory, i.e. lasting for more than a fleeting instant or seconds. The medium may be memory, such as RAM or ROM, a cd or dvd, flash memory, or the like.

Various aspects of methods, systems, devices, computer-readable media, etc. are described herein. A summary of some of the aspects is provided below.

In a first aspect, a method comprises (i) identifying a patient for which a blood fluid removal session is indicated; and (ii) chronically monitoring an indicator of blood electrolyte concentration or blood pH of the patient via an implantable sensor device.

A second aspect is a method of the first aspect, further comprising (i) determining whether the monitored indicator crosses a predetermined threshold; and (ii) alerting the patient if the indicator is determined to cross the threshold.

A third aspect is a method of the second aspect, further comprising alerting a healthcare provider if the indicator is determined to cross the threshold.

A fourth aspect is a method of the first aspect, further comprising determining an appropriate electrolyte concentration or buffer concentration for a fluid to be used in a blood fluid removal session based on the monitored indicator.

A fifth aspect is a method of the fourth aspect, wherein the fluid to be used in the blood fluid removal session comprises dialysate fluid.

A sixth aspect is a method of the fifth aspect, wherein the fluid to be used in the blood fluid removal session comprises replacement fluid.

A seventh aspect is a method of any of aspects 1-6, further comprising transmitting data regarding the monitored indictor to a blood fluid removal device, or control electronics configured to control a blood fluid removal device, wherein the blood fluid removal device or control electronics determines the appropriate electrolyte concentration or buffer concentration.

An eighth aspect is a method of any of aspects, 1-7, wherein the monitoring comprises monitoring the indicator via an implantable sensor.

A ninth aspect is a method of aspect 8, further comprising monitoring the indicator via an external sensor, and calibrating the implantable sensor based on data acquired from the external sensor.

A tenth aspect is a method of aspect 9, wherein the monitoring via the external sensor occurs during a blood fluid removal session, and wherein the calibrating occurs during a blood fluid removal session.

An eleventh aspect is a method comprising: (i) chronically monitoring, via an implantable sensor, an indicator of blood electrolyte concentration or blood pH of the patient during the blood fluid removal session; and (ii) initiating blood fluid removal procedure for a patient in need thereof, wherein the procedure comprises use of a dialysate fluid and a dialysis membrane, as at least a part of a blood fluid removal medium, across which electrolytes may be exchanged between blood and dialysate fluid, wherein the concentration of electrolyte in the dialysate fluid is based on a value of the monitored indicator.

A twelfth aspect is a method comprising: (i) chronically monitoring, via an implantable sensor, an indicator of blood electrolyte concentration or blood pH of the patient during the blood fluid removal session; and (ii) initiating blood fluid removal procedure for a patient in need thereof, wherein the procedure comprises use of a dialysate fluid and a dialysis membrane, as at least a part of a blood fluid removal medium, across which electrolytes may be exchanged between blood and dialysate fluid, wherein the rate of flow of the dialysate fluid or the blood is based on a value of the monitored indicator.

EXAMPLE

The following prophetic example is presented to provide guidance as to how to acquire and interpret data from an implantable sensor configured to monitor pH or electrolytes in blood of a patient for use in methods or devices as described in the DETAILED DESCRIPTION above. It will be understood that the prophetic example provided herein in only one suitable way for monitored data to be acquired and interpreted in accordance with the general principles disclosed herein.

For this prophetic example, an implantable transducer of a sensor that is configured to detect the presence of a specific ion species (e.g., $K^+$, $Na^+$ of $H^+$) is calibrated by placement in blood of known concentrations of the ion species. A sensor response profile for the various concentrations of ion species is then recorded and entered into memory, which can be memory of the sensor device or a device in communication with the sensor. Once calibrated, the sensor, or transducer, may then be placed within a blood vessel of the patient (e.g., using a stent-like, or Medtronic, Inc. ALPS-like device) to monitor the ion species in the patient's blood.

The sensor may be recalibrated occasionally. For example, blood can be withdrawn from the patient and lab tests may be performed to determine the actual concentration of the ionic species in the blood. The actual value of the ionic species may then be communicated to the sensor, which can then re-calibrate, if necessary, based on the actual value and the initial calibration curve. In some cases, the sensor may include an internal reference standard, such as with Medtronic, Inc.'s Bravo® pH sensor, which may be used to calibrate the sensor from time to time.

In any case, once the sensor is properly calibrated, its readings with regard to amount ionic species may be trusted. These readings can then be reliably used in accordance with the teachings provided herein.

Thus, systems, devices and methods for CHRONIC pH OR ELECTROLYTE MONITORING are described. Those skilled in the art will recognize that the preferred embodiments described herein may be altered or amended without departing from the true spirit and scope of the disclosure, as defined in the accompanying claims.

What is claimed is:

1. A method for a blood fluid removal device, comprising the steps of:
   (1) chronically monitoring a blood electrolyte concentration or blood pH of a patient via an implantable sensor device; and
   (2) transmitting data regarding the monitored blood electrolyte concentration or blood pH to the blood fluid removal device selected from the group consisting of an ultrafiltration device, a hemofiltration device, a hemodiafiltration device, and a peritoneal dialysis device, or to control electronics configured to control the blood fluid removal device,
   wherein the blood fluid removal device or control electronics determines an appropriate electrolyte concentration or buffer concentration of a fluid to be used in the blood fluid removal device based on the monitored blood electrolyte concentration or blood pH during a blood fluid removal session, and controls flow of a concentrate from one or more concentrate sources into the fluid to achieve the appropriate electrolyte concentration or buffer concentration.

2. The method of claim 1, further comprising
   (i) determining whether the monitored blood electrolyte concentration or blood pH crosses a predetermined threshold; and
   (ii) alerting the patient if the blood electrolyte concentration or blood pH is determined to cross the threshold.

3. The method of claim 2, further comprising alerting a healthcare provider if the blood electrolyte concentration or blood pH is determined to cross the threshold.

4. The method of claim 1, wherein the fluid to be used in the blood fluid removal device comprises dialysate fluid.

5. The method of claim 1, wherein the fluid to be used in the blood fluid removal device comprises replacement fluid.

6. The method of claim 1, further comprising monitoring the blood electrolyte concentration or blood pH via an external sensor, and calibrating the implantable sensor based on data acquired from the external sensor.

7. The method of claim 6, wherein the monitoring via the external sensor occurs during a blood fluid removal session, and wherein the calibrating occurs during a blood fluid removal session.

8. A method for a blood fluid removal device comprising:
   chronically monitoring, via an implantable sensor, a blood electrolyte concentration or blood pH of a patient during a blood fluid removal session; and
   initiating a blood fluid removal procedure for a patient in need thereof, wherein the procedure comprises use of a dialysate fluid and a dialysis membrane, as at least a part of a blood fluid removal medium, across which electrolytes may be exchanged between blood and dialysate fluid, and
   transmitting data regarding the monitored blood electrolyte concentration or blood pH to the blood fluid removal device, containing the blood fluid removal medium, wherein the blood fluid removal device is selected from the group consisting of an ultrafiltration device, a hemofiltration device, a hemodiafiltration device, and a peritoneal dialysis device or to control electronics configured to control a blood fluid removal device,
   wherein the blood fluid removal device or control electronics determines the appropriate electrolyte concentration or buffer concentration in the dialysate fluid based on a value of the monitored blood electrolyte concentration or blood pH during the blood fluid removal session, and the blood fluid removal device or control electronics controls flow of a concentrate from one or more concentrate sources into the dialysate fluid to achieve the appropriate electrolyte concentration or buffer concentration, and wherein the data is transmitted wirelessly.

9. A method for a blood fluid removal device comprising:

chronically monitoring, via an implantable sensor, a blood electrolyte concentration or blood pH of a patient during a blood fluid removal session; and initiating a blood fluid removal procedure for a patient in need thereof, wherein the procedure comprises use of a dialysate fluid and a dialysis membrane, as at least a part of a blood fluid removal medium, across which electrolytes may be exchanged between blood and dialysate fluid, wherein the rate of flow of the dialysate fluid or the blood is based on a value of the monitored blood electrolyte concentration or blood pH; and transmitting data regarding the monitored blood electrolyte concentration or blood pH to the blood fluid removal device, containing the blood fluid removal medium, wherein the blood fluid removal device is selected from the group consisting of an ultrafiltration device, a hemofiltration device, a hemodiafiltration device, and a peritoneal dialysis device, or to control electronics configured to control the blood fluid removal device, wherein the blood fluid removal device or control electronics determines an appropriate electrolyte concentration or buffer concentration in the dialysate fluid during the blood fluid removal session and controls flow of a concentrate from one or more concentrate sources into the dialysate fluid to achieve the appropriate electrolyte concentration or buffer concentration, and wherein the data is transmitted wirelessly.

10. The method of claim 1, wherein the flow of concentrate from the one or more concentrate sources is controlled by one or more pumps and one or more valves in fluid communication with the one or more concentrate sources.

11. The method of claim 1, wherein a patient for which a blood fluid removal session is indicated is identified prior to monitoring the blood electrolyte concentration or blood pH.

12. The method of claim 1, wherein the step of determining an appropriate electrolyte concentration is performed by an implanted transducer.

13. The method of claim 1, wherein the blood fluid removal device is an implantable blood fluid removal device.

14. The method of claim 1, wherein the blood fluid removal device is a wearable blood fluid removal device.

15. The method of claim 1, wherein the blood fluid removal device or control electronics determines an appropriate buffer concentration buffer is selected from the group consisting of bicarbonate, acetate, lactate, citrate, amino acid, and protein buffers.

16. The method of claim 1, wherein the electrolyte is selected from the group consisting of sodium, potassium, calcium, and chloride.

17. The method of claim 1, wherein the step of chronically monitoring blood electrolyte concentration comprises chronically monitoring multiple blood electrolyte concentrations, and wherein the step of determining an appropriate electrolyte concentration comprises determining an appropriate electrolyte concentration for each of the multiple electrolytes.

18. The method of claim 1, further comprising the step of initiating a blood fluid removal session; and wherein the blood fluid removal device or control electronics determines an appropriate electrolyte concentration or buffer concentration of the fluid to be used in the blood fluid removal device based on the blood electrolyte concentration or blood pH during the blood fluid removal session.

19. The method of claim 1, wherein the blood fluid removal device or control electronics determines an appropriate dialysate flow rate based on the blood electrolyte concentration or blood pH.

20. The method of claim 1, wherein the blood fluid removal device or control electronics determines an appropriate blood flow rate based on the blood electrolyte concentration or blood pH.

21. The method of claim 1, wherein the data is transmitted wirelessly.

22. The method of claim 1, wherein the blood pH is monitored.

23. The method of claim 1, wherein at least a portion of the chronic monitoring of the blood electrolyte concentration or blood pH of the patient comprises monitoring prior to a blood removal session.

24. The method of claim 1, wherein the blood fluid removal device or control electronics determines an appropriate pH of the fluid to be used in treatment based on the blood electrolyte concentration or blood pH during a blood fluid removal session.

* * * * *